(12) United States Patent
Collins

(10) Patent No.: US 6,733,517 B1
(45) Date of Patent: May 11, 2004

(54) ANGLING INTRODUCER SHEATH FOR CATHETER HAVING TEMPERATURE CONTROL SYSTEM

(75) Inventor: Kenneth A. Collins, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 10/171,346

(22) Filed: Jun. 12, 2002

Related U.S. Application Data
(60) Provisional application No. 60/298,020, filed on Jun. 13, 2001.

(51) Int. Cl.[7] .................................................. A61F 7/00
(52) U.S. Cl. ...................................... 607/105; 606/108
(58) Field of Search ................................ 607/104, 105, 607/106, 107; 606/108, 198

(56) References Cited

U.S. PATENT DOCUMENTS 5,676,688 A * 10/1997 Jaker et al. .................. 606/195
6,562,049 B1 * 5/2003 Norlander et al. ........... 606/108

* cited by examiner

*Primary Examiner*—Roy D. Gibson
(74) *Attorney, Agent, or Firm*—John L. Rogitz

(57) ABSTRACT

An introducer sheath for a catheter includes an angling membrane formed at its distal end and an inflate/deflate mechanism formed at its proximal end to deploy the angling membrane. The sheath further includes two hollow body shafts connected at the distal end and can concentrically accommodate the catheter inside the shafts for positioning the catheter in a patient's vena cava system. The introducer sheath is used for positioning at least a portion of the catheter in the inferior vena cava from a chest or neck insertion point. Once the catheter's heat exchange elements are firmly positioned in the inferior vena cava, the angling membrane can be deflated and the angling introducer sheath removed leaving the catheter in place.

17 Claims, 5 Drawing Sheets

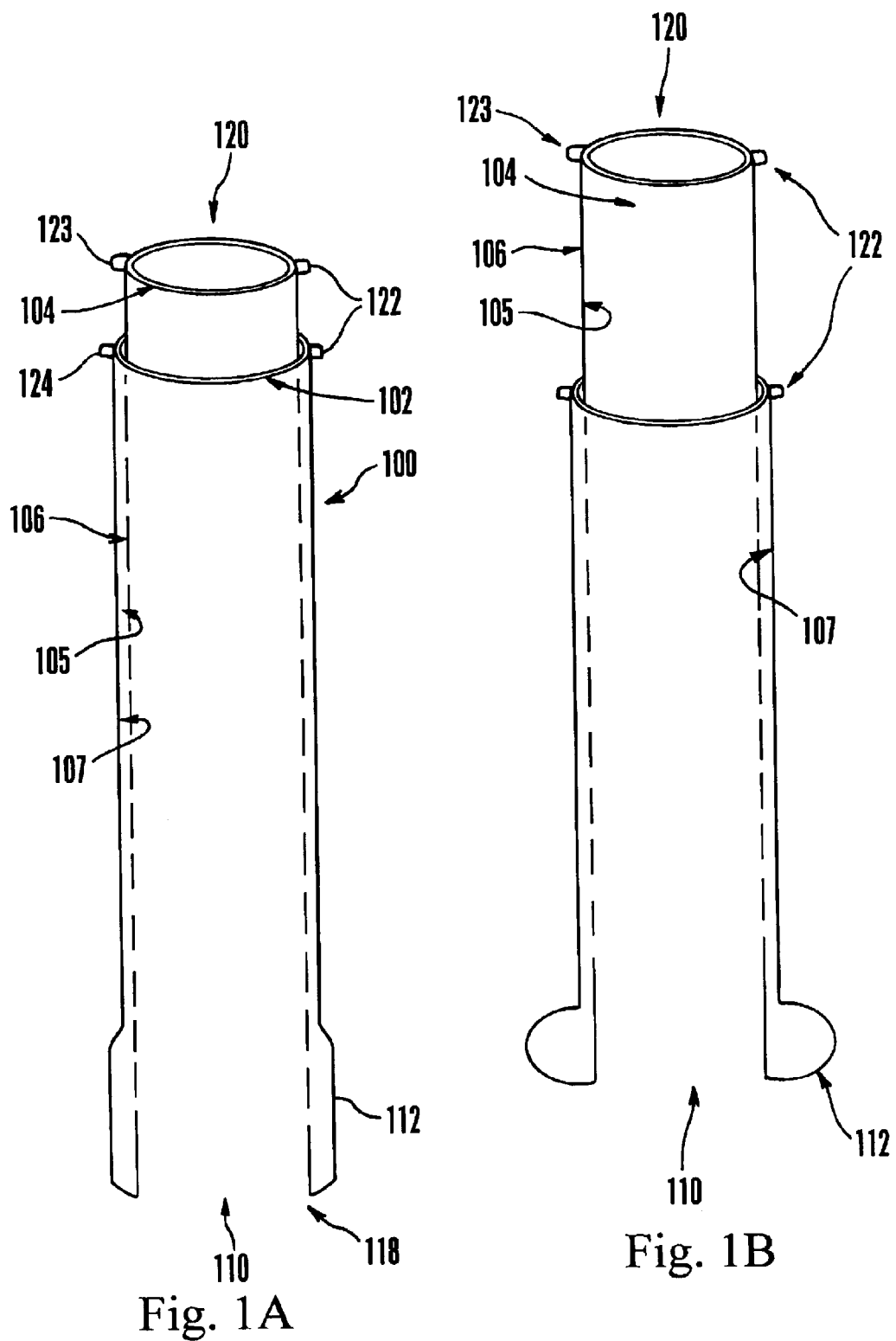

Simplified View Not Drawn To Proportion

ANGLING INTRODUCER SHEATH FOR CATHETER HAVING TEMPERATURE CONTROL SYSTEM

This application claims the benefit of Provisional application Ser. No. 60/298,020, filed Jun. 18, 2001.

BACKGROUND OF THE INVENTION

1. Field of the Invention

The invention relates to introducer sheaths for catheters used for access to the central venous blood supply of a patient while providing a means for cooling or warming a patient.

2. Description of Related Art

Catheters such as central venous line catheters are typically used in ICU (intensive care unit) patients, for example, in patients who have suffered a stroke or other brain traumatic event, or who need cardiac bypass surgery. The central venous line catheters are typically about 8.5–12 French in diameter and consist of a soft, flexible multi-lumen structure extending 8–12 inches. The catheters are usually introduced using an introducer sheath or a guidewire through the subclavian or jugular veins, and less preferably in the femoral vein of the patient. The subclavian, jugular and femoral veins serve to provide an easy access to the patient's central blood supply via the central venous system. In this manner general access to the central blood supply is gained, enabling for example delivery of drugs, infusion fluids or nutrition, along with the gathering of patient blood for blood gas analysis and the like. Typically, the catheter's distal end is lodged in the superior vena cava. The superior vena cava is easier to access from a neck or chest insertion point than the inferior vena cava since the superior vena cava is located above the right atrium. If access is to be gained to the inferior vena cava from the subclavian or jugular veins, the catheter must bypass the entry to the right atrium. Inadvertently lodging a catheter in the right atrium can be fatal. However, lodging a catheter's heat exchange element in the inferior vena cava can be advantageous because the volume of blood returning through the inferior vena cava is about 66% to 75% of the total blood volume of a patient compared to a blood volume of about 25% to 34% in the superior vena cava.

In many patients, such as ICU patients or head trauma patients, fever is a common occurrence and its onset can exacerbate detrimental effects. Conventional therapies to control fever include treatment with acetaminophen (Tylenol®), cooling blankets, ice water bladder lavages, and ice baths. All of these approaches to cooling a patient require excessive time to cool the patient. Moreover, prior methods do not provide for precise control of patient cooling. As recognized herein, to optimize the advantage of cooling a patient, it is important to cool the patient relatively quickly in a controlled fashion.

Similarly, a post surgery patient may require active rewarming to prevent shivering. Postoperative shivering increases metabolic rate and potentially may lead to myocardial ischemia among other things. Thus, prevention of postoperative shivering is desirable. The present invention recognizes these problems and provides the solutions discussed below to one or more of them.

BRIEF SUMMARY OF THE INVENTION

The present invention overcomes the deficiencies of the prior art by adapting an introducer sheath with an angling membrane at its distal tip and a mechanism to inflate and deflate the angling membrane. The present introducer sheath is used for positioning a catheter in the inferior vena cava from a chest or neck insertion point. It includes a hollow body defining a proximal end, a distal end positionable in a patient, at least one catheter placement lumen extending therebetween, an angling membrane and an inflation/deflation mechanism. Once the catheter's heat exchange elements are firmly positioned in the inferior vena cava, the angling membrane can be deflated and the angling introducer sheath removed.

The catheter can be a catheter having an internal circulating fluid as disclosed in U.S. Pat. Nos. 6,126,684 and 5,837,003, incorporated herein by reference, or other similar device. In one embodiment, the catheter is a central venous line catheter which can include heat exchange elements to actively exchange heat with the body of the patient to thereby raise or lower body temperature as required. The catheter is provided with a heat exchange element disposed in heat exchange relationship with the blood of the patient. The heat exchange element houses a circulating fluid therein, with the fluid being automatically cooled or warmed exteriorly of the patient's body in accordance with a patient temperature feedback scheme.

The access, typically through the subclavian or jugular veins, is to the central blood supply, via the central venous system, and is therefore particularly expedient, permitting efficient cooling or warming of patient body temperature. The term central venous system generally relates to the portion of the venous system which returns blood to the right heart, including the superior and inferior vena cava. The heat exchange relationship between the catheter and the central venous system of the patient can be maintained for a prolonged duration, for example, from about one hour to about twenty-nine days.

The catheter comprises a tubular structure defining a plurality of lumens. At least two of these lumens convey heat exchange fluid to a heat exchange element disposed at a distal, implantable end of the catheter, while the rest of the lumens serve to provide access to the central blood supply of the patient. The heat exchange element is in fluid communication with a temperature control module via a tubing set which conveys the heat exchange fluid between the components. The temperature control unit, comprising a cooling and/or a heating device, operates in conjunction with a temperature controller to heat or cool the heat exchange fluid depending on a sensed temperature of the patient.

The invention thus provides for controlling patient temperature using a neck or chest insertion point to insert a central venous line catheter having a heat exchange element and to position the catheter's heat exchange elements in the inferior vena cava. The catheter is provided with one or more lumens for providing access to the central blood supply of the patient, and with additional lumens for communicating heat exchange fluid to the heat exchange elements. Heat exchange fluid temperature is controlled through a feedback loop in which patient temperature is sensed and used to control a temperature control unit comprising a heating device and/or a cooling device in heat exchange relationship with the heat exchange fluid. A tubing-set transports the heat exchange fluid between the catheter and the temperature control unit, with a pump serving to circulate the fluid in a closed fluid circuit.

BRIEF DESCRIPTION OF THE SEVERAL VIEWS OF THE DRAWING(S)

Many advantages of the present invention will be apparent to those skilled in the art with a reading of this specification in conjunction with the attached drawings, wherein like reference numerals are applied to like elements and wherein:

FIG. 1a is a schematic side view of an angling introducer sheath in the nondeployed configuration in accordance with the invention;

FIG. 1b is a schematic side view of an angling introducer sheath in the deployed configuration in accordance with the invention;

DETAILED DESCRIPTION OF THE INVENTION

Figure 3:
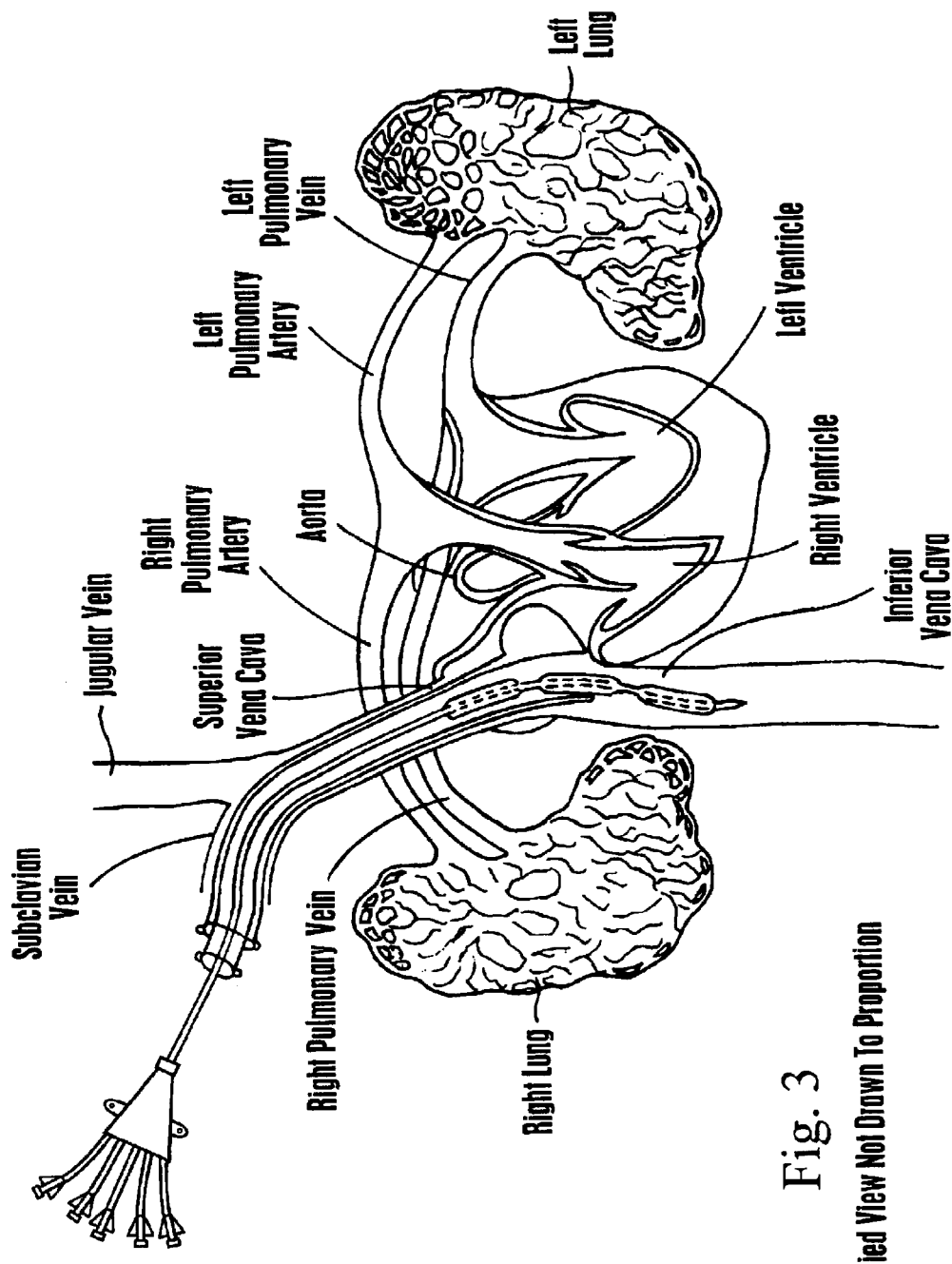
FIG. 3 is a perspective view of an embodiment of the angling introducer sheath and a central venous line catheter operatively disposed in the inferior vena cava in accordance with the present invention.

FIG. 1a shows an angling introducer sheath 100 in the non-deployed configuration in accordance with the invention. The angling introducer sheath 100 includes a proximal tip 120, a distal tip 110, an angling membrane 112 at the distal end 110 and an inflate/deflate mechanism 122 to inflate and deflate the angling membrane 112 at the proximal end 120. The angling introducer sheath 100 includes two hollow shafts 102 and 104 which connect through the angling membrane 112 to form a continuous piece. Second shaft 104 has a hollow center and is partially lodged inside first shaft 102 which also has a hollow center. The present introducer sheath 100 is used for positioning at least a portion of a catheter in the inferior vena cava from a chest or neck insertion point. The introducer sheath 100 is first inserted through the subclavian or jugular vein until its distal edge 110 reaches entry way to the right atrium (FIG. 3). To deploy the angling mechanism 112, the second shaft 104 is pulled in the proximal direction to cause the angling mechanism 112 to bulge. FIG. 1b is a schematic side view of an angling introducer sheath 100 in the deployed configuration in accordance with the invention.

Once the sheath 100 is deployed, the catheter 20 (FIGS. 2a–2c) can be inserted into the second shaft 104 to reach pass the right atrium entry to the inferior vena cava (FIG. 3). At least one of the catheter's heat exchange elements 30 is positioned in the inferior vena cava. Once the catheter position is secured, the angling membrane 112 can be deflated by pushing the second shaft 104 in the distal direction. Once deflated, the angling introducer sheath 100 can be removed from the patient while leaving the catheter 20 inside the patient's central venous system.

Figure 2A:
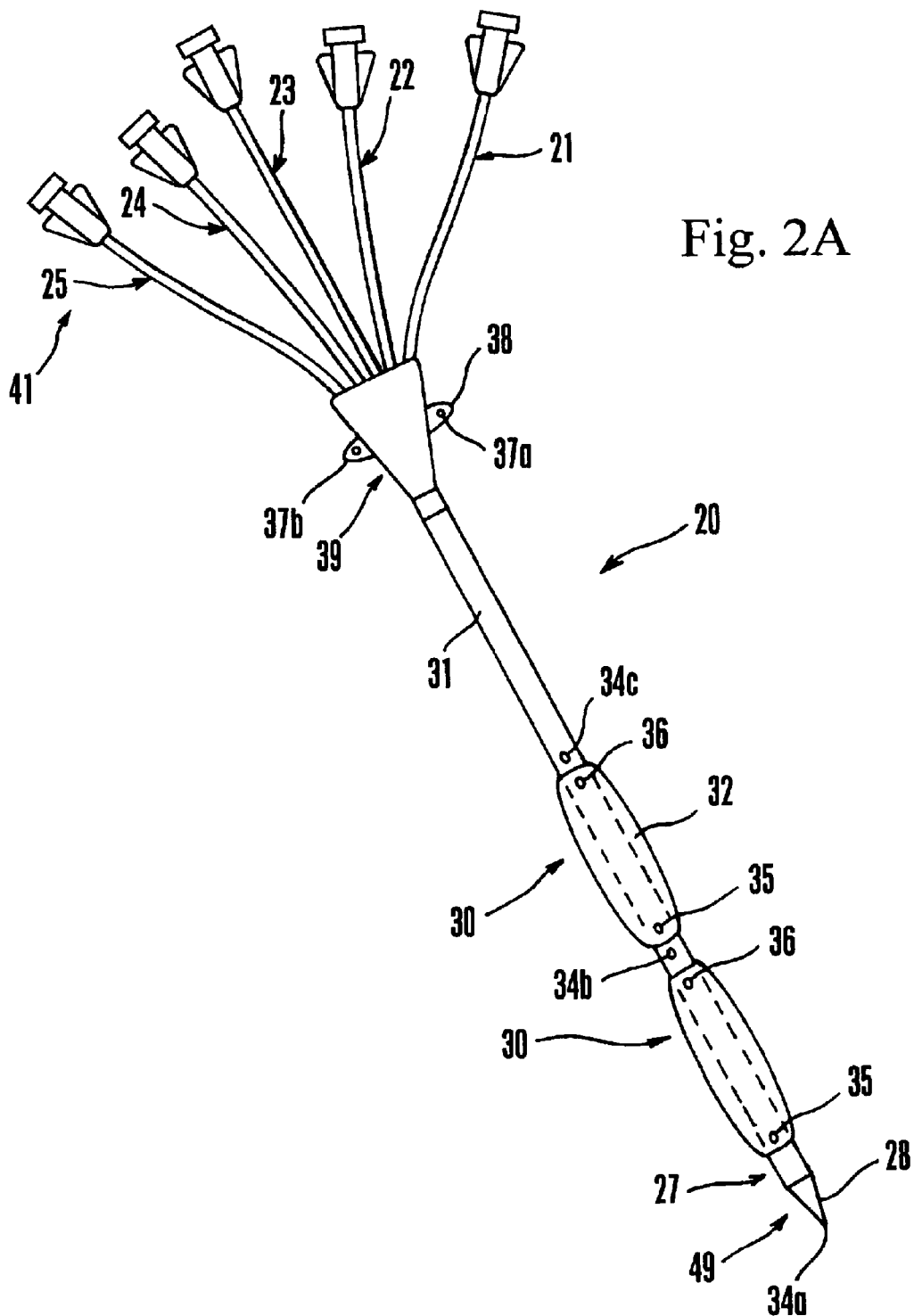
FIG. 2a is a schematic side view of a central venous line catheter in accordance with the invention.
Figure 2B:
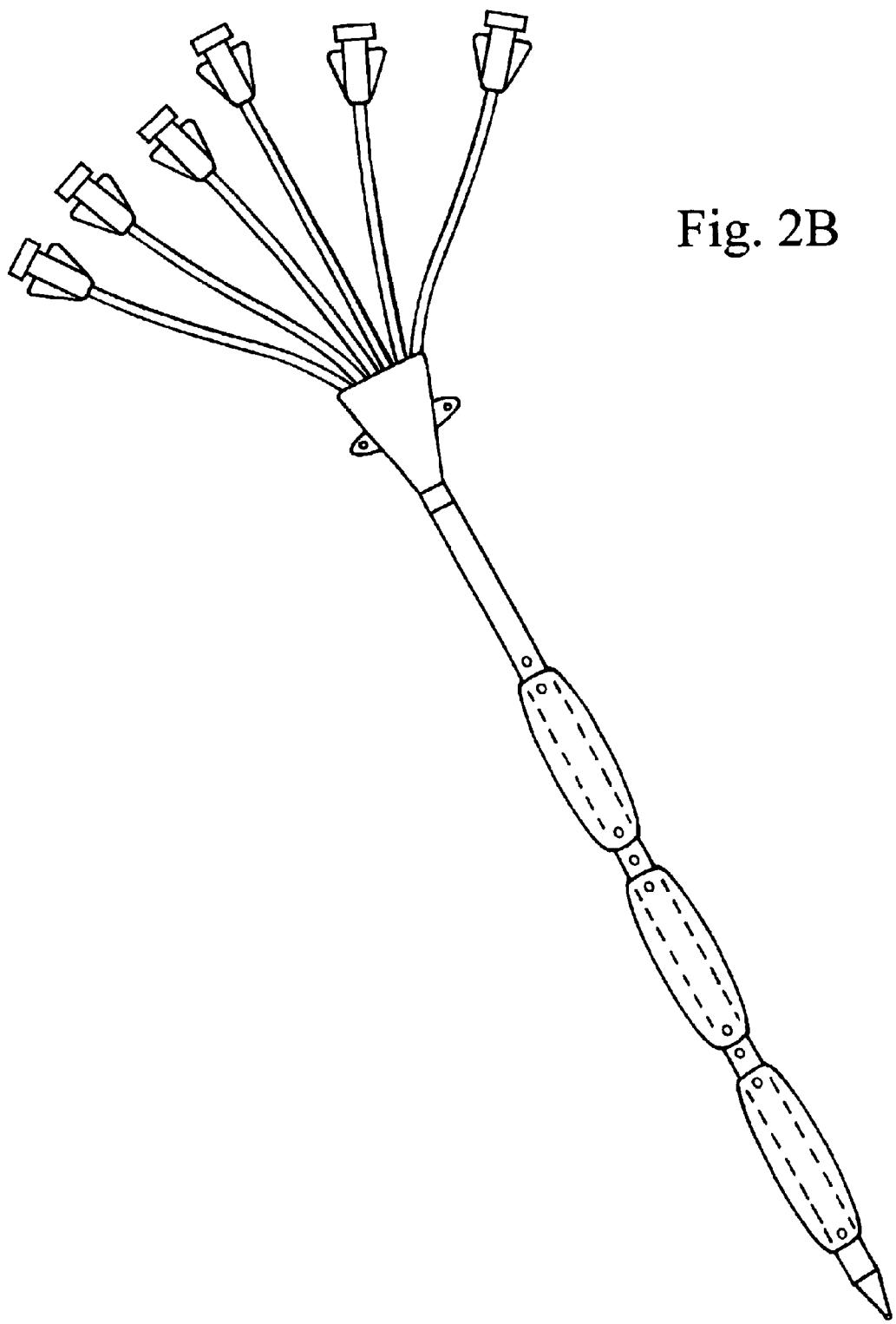
FIG. 2b is a schematic side view of a second embodiment of a central venous line catheter in accordance with the invention.
Figure 2C:
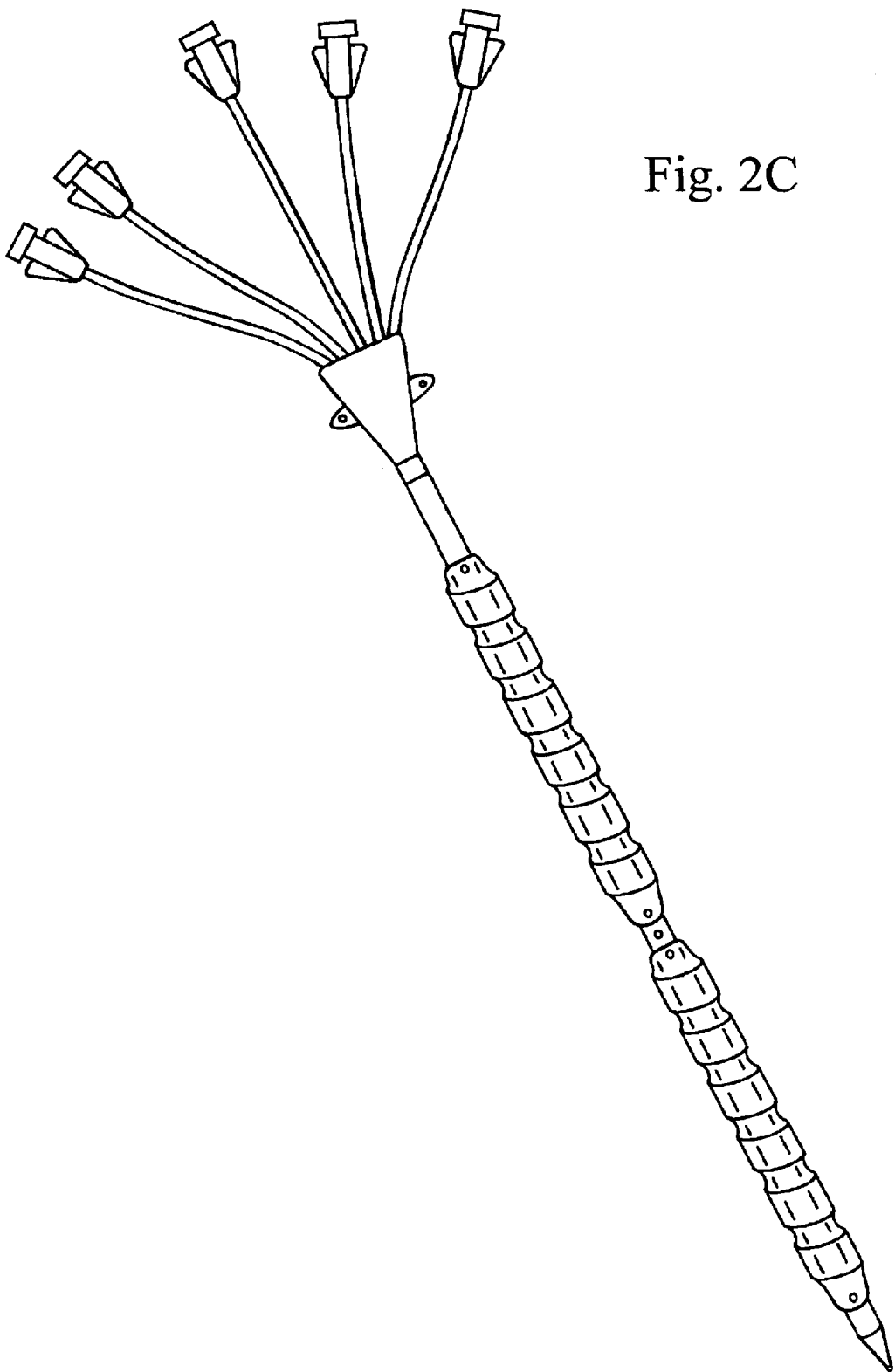
FIG. 2c is a schematic side view of a third embodiment of a central venous line catheter in accordance with the invention.

FIGS. 2a–2c show a catheter 20 that is a multi-lumen device, with at least two of the lumens 21–22 being dedicated to heat exchange fluid flow to and from a heat exchange element of the catheter. The other lumen(s) 23–25 can have different uses, such as fluid infusion, drug delivery or blood extraction/monitoring, and so on, depending on the particular application. The preferred number of lumens is 3 to 5, although other numbers are contemplated. The catheter 20 is a substantially elongate structure of generally cylindrical shape adapted for insertion into the body of a patient, preferably into the subclavian or jugular veins. Catheter 20 is formed of any known polymer material 26 defining its various lumens 21, 22, 23, 24 and 25. A preferred material is polyurethane, although other materials, such as nylon, polyethylene and PEBAX, can also be used. Considerations in selecting the appropriate material 26 include biocompatibility, flexibility, temperature change compatibility, and resistance to buckling.

At its distal, implantable end portion 27, catheter 20 is provided with a heat exchange element such as fluid-carrying inflatable balloon 30 that is radially disposed around the width of the catheter. Balloon 30 is disposed in the vicinity of flexible tip 28 and can be formed from a piece of sheet material 29 or extruded tubing formed into a molded balloon of the desired shape and size and then bound or otherwise fixed to the shaft 31 to form a cavity 32. As illustrated, balloon 30 is shown to have a significantly larger diameter than shaft portion 31 of the catheter. For example, it is contemplated that in some applications the diameter of the inflated balloon will be more than three times that of shaft 31. In one preferred embodiment, the balloon diameter is four millimeters to ten millimeters (4 mm–10 mm). Preferably, the diameter of the balloon is selected to be no more than 30%–75% of the diameter of a typical vena cava. It is to be appreciated that in some cases it may be desirable to maximize the dimension of the shaft 31 in order to facilitate heat exchange fluid flow. This will also minimize the volume of fluid in the balloon 30 and promote a more rapid heat exchange. It will be further appreciated that myriad balloon shapes can be utilized with the invention, including but not limited to spiral or fluted shapes, as disclosed in FIG. 2c. The particular shape selected would depend on the application and the desired heat exchange and other characteristics. In one preferred embodiment, the balloon 30 is made of urethane, nylon, or PET and is thin-walled, i.e., the balloon 30 has a wall thickness of less than three mils, and more preferably less than one and one-half mils. Also, the balloon 30 preferably is coated with an antimicrobial substance, as well as an anticlot substance, such as heparin.

It is to be understood that the balloon 30 can extend the entire length of the portion of the central venous catheter that is intubated in the patient. Typically, this length is about 15 cm to 20 cm depending on the height of the patient. Under such circumstances, the diameter of the balloon need not be larger than the diameter of a conventional central venous catheter, e.g., the diameter of the balloon can be 12 French, 10 French, or even as small as 7.5 French. More broadly, the balloon diameter, when the balloon extends along the entire length of the intubated portion of the catheter, can be 5–13 French. In an arrangement where multiple balloons are used as detailed below, these balloons can cover the entire length of the intubated portion of the catheter. That is, two balloons of about 7.5 cm each can be used, or three 5 cm balloons, etc. Additionally, depending on the height of the patient, two balloons of about 8 cm and one balloon of about 5 cm may be used. It can be appreciated that a variety of balloon sizes can be used depending on the patient's height and size.

A pair of lumens 21 and 22 are formed in catheter 20, with lumen 21 serving as an inflow channel supplying balloon 30 with heat exchange fluid which is circulated through the catheter 20, while lumen 22 serves as an outflow channel returning the heat exchange fluid from the balloon 30 to the catheter. The particular heat exchange fluid selected is preferably biocompatible to avoid harm to the patient in the event of inadvertent rupture. Candidate materials include sterile saline water and carbon dioxide gas, although other fluids having suitable viscosity, heat exchange and material compatibility characteristics can also be used. While less desired because it is not biocompatible, freon can alternatively be used.

Balloon 30 is in fluid communication with lumens 21 and 22 via a plurality of ports such as inlet port 35 and outlet port 36. Heat exchange fluid circulated in catheter 20 passes from lumen 21 into cavity 32 through inlet port 35, then out of cavity 32 to lumen 22 through outlet port 36. While in the cavity 32, the heat exchange fluid, which is remotely cooled outside the central venous line catheter 20, serves to provide a cold temperature fluid on the inner surface of the sheet material 29 which forms the walls of balloon 30. With a body fluid, such as blood, flowing exteriorly of the balloon 30, heat transfer occurs across the sheet material 29, effectively cooling or heating the body of the patient. To that end, inlet port 35 is positioned distally of outlet port 36.

In order to facilitate fluid flow in and out of cavity 32 of balloon 30, outlet port 36 can be made larger than inlet port 35 to reduce the resistance encountered by the heat exchange fluid as it exits the balloon 30. This relative size difference becomes particularly important when multiple balloons are provided in catheter 20 as is contemplated in accordance with the embodiments shown in FIGS. 2a–2c. Specifically, although described in terms of a single balloon 30, it will be appreciated that several such balloons can be provided, disposed axially along the length of shaft 31, as shown in FIGS. 2a–2c. One advantage of a multiple balloon configuration is that the flow and temperature of the heat exchange fluid can be more easily controlled along the entire length of the heat exchange region of the catheter 20. Realizing that the heat exchange fluid will be coolest or hottest prior to entering into heat exchange with the blood, and warmest or coolest after that heat exchange, one can advantageously control not only the velocity and volume of flow, but also the direction of flow within each of the balloons 30. Another advantage of a multiple balloon design is the ability of the catheter to bend and flex when placed in a curved vasculature.

Catheter 20 is also provided with two or three infusion lumens 23, 24 and 25. Lumens 23, 24 and 25 can serve a multiplicity of functions, including infusion of drugs such as chemotherapy, fluids and nutrition, access to syringes for sampling, accommodation of various sensors such as thermistors to monitor the patient, and blood extraction/monitoring functions, thus generally providing access to the central blood supply as dictated by the particular application. Additionally, central lumen 23 may be made of a different diameter than side lumens 24 and 25 in order to better support various functions, for instance the sensors. The lumens extend substantially the full length of catheter 20, from proximal end portion 41 to distal end portion 49. The number of lumens provided can be varied depending on the particular application.

It will also be appreciated that the heat exchange element does not necessarily need to be in the form of a balloon such as balloon 30. Rather, arrangements such as an array of flexible hollow fibers through which the heat exchange fluid is circulated can also be used, thus affording greater surface area for heat exchange interaction. Additionally, other heat exchange elements such as those disclosed in U.S. Pat. No. 5,837,003, incorporated herein by reference, or other similar device may be used.

Additionally, as best seen in FIGS. 2a–2c, the catheter 20 includes an anchor 39 configured for affixing the catheter 20 to the patient. More specifically, in one intended embodiment, the anchor 39 is established by a suture fitting 38. The suture fitting 38 can be made integrally with the catheter 20, or it can be made as a separate plastic fitting and surroundingly engaged with the catheter 20. As shown, the suture fitting 38 includes two eyes 37a, 37b through which sutures can be positioned and engaged with the patient's skin or with a bandage or tape or other structure that has been fastened to the patient. As understood herein, an anchor 39 is desirable in a central venous catheter to hold the catheter on the patient, because a central venous catheter typically is intended for prolonged indwelling.

The above are exemplary modes of carrying out the invention and are not intended to be limiting. It will be apparent to one of ordinary skill in the art that modifications thereto can be made without inventive departure from the spirit and scope of the invention as set forth in the following claims.

What is claimed:

1. An angling introducer sheath comprising:
    a first hollow shaft with a first section and a second section, the second section includes an angling membrane;
    a second hollow shaft with a distal section and a proximal section, the distal section connected to the angling membrane to form a continuous piece with the first shaft wherein the second shaft is partially lodged inside the first shaft.

2. The angling introducer sheath of claim 1 wherein the angling membrane includes an expandable/contractable cavity.

3. The angling introducer sheath of claim 2 further comprising a first expand/contract mechanism connected to the first section.

4. The angling introducer sheath of claim 3 further comprising a second expand/contract mechanism connected to the proximal section.

5. The angling introducer sheath of claim 2 further comprising at least one expand/contract mechanism to expand or to contract the expandable/contractable cavity.

6. A kit comprising
    an angling introducer sheath having a first hollow shaft with a first section and a second section, the second section includes an angling membrane, and having a second hollow shaft with a distal section and a proximal section, the distal section connected to the angling membrane to form a continuous piece with the first shaft wherein the second shaft is partially lodged inside the first shaft;
    a heat exchange catheter with at least one heat exchange member, the catheter partially lodged inside the second shaft.

7. The kit of claim 6 wherein the catheter further comprises a catheter body with a plurality of lumens for fluid communication with the heat exchange member.

8. The kit of claim 7 wherein the catheter body comprises a plurality of infusion lumens.

9. The kit of claim 7 wherein a fluid is circulated from at least one of the plurality of lumens to the heat exchange member then to at least one other of the plurality of lumens in a closed loop.

10. The kit of claim 6 wherein the heat exchange member is at least one balloon.

11. A method of inserting a catheter into the inferior vena cava through a neck or chest entry point comprising the steps of:
    inserting an angling introducer sheath through a neck or chest entry insertion point to partially lodge in the inferior vena cava of a patient, wherein the angling introducer sheath comprises at least two hollow shafts and an angling membrane with an inflatable/deflatable cavity;

inflating, the inflatable/deflatable cavity;

inserting a catheter into at least one of the at least two hollow shafts, wherein the catheter at least partially lodges in the inferior vena cava of the patient;

deflating the inflatable/deflatable cavity;

removing the angling introducer sheath from the patient while leaving the catheter at least partially lodged in the inferior vena cava of the patient.

12. The method of claim 11 wherein the catheter comprises at least one heat exchange member for exchanging heat with the blood of the patient flowing through the inferior vena cava.

13. The method of claim 12 further comprising the step of circulating a coolant through the heat exchange member.

14. The method of claim 11 wherein the catheter comprises
a catheter body with a distal end and a proximal end;
at least one heat exchange member on the catheter body;
a supply lumen and a return lumen for fluid communication with at least one heat exchange member; and
a plurality of infusion lumens on the distal end for infusion of fluids or extraction of fluids.

15. The method of claim 14 further comprising the step of infusing one of medication, nutrient or coolant into the inferior vena cava of the patient.

16. The method of claim 14 further comprising the step of extracting body fluid from the patient.

17. The method of claim 14 further comprising the step of taking diagnostic measurements of the patient though a probe inserted through at least one infusion lumen.

* * * * *